(12) United States Patent
Schwardt et al.

(10) Patent No.: US 7,955,339 B2
(45) Date of Patent: Jun. 7, 2011

(54) LOW-COMPLIANCE EXPANDABLE MEDICAL DEVICE

(75) Inventors: Jeffrey D. Schwardt, Palo Alto, CA (US); Andrea Leung, Milpitas, CA (US); Richard W. Layne, Phoenix, AZ (US)

(73) Assignee: Kyphon SARL, Neuchatel (CH)

( * ) Notice: Subject to any disclaimer, the term of this patent is extended or adjusted under 35 U.S.C. 154(b) by 709 days.

(21) Appl. No.: 11/438,693

(22) Filed: May 23, 2006

(65) Prior Publication Data

US 2007/0050035 A1   Mar. 1, 2007

Related U.S. Application Data

(60) Provisional application No. 60/683,803, filed on May 24, 2005.

(51) Int. Cl.
*A61B 17/66* (2006.01)
(52) U.S. Cl. ...................................................... 606/105
(58) Field of Classification Search .................. 600/207; 606/105, 192; 623/17.12, 17.11, 17.13–17.16
See application file for complete search history.

(56) References Cited

U.S. PATENT DOCUMENTS

| | | | |
|---|---|---|---|
| 4,083,369 A | 4/1978 | Sinnreich | |
| 4,313,434 A | 2/1982 | Segal | |
| 4,327,736 A | 5/1982 | Inoue | |
| 4,969,888 A | 11/1990 | Scholten et al. | |
| 5,108,404 A | 4/1992 | Scholten et al. | |
| 5,156,612 A | 10/1992 | Pinchuk et al. | |
| 5,254,091 A | 10/1993 | Aliahmad | |
| 5,331,975 A | 7/1994 | Bonutti | |
| 5,423,850 A | 6/1995 | Berger | |
| 5,439,447 A | 8/1995 | Miraki | |
| 5,549,679 A | 8/1996 | Kuslich | |
| 5,972,015 A | 10/1999 | Scribner et al. | |
| 6,066,154 A | 5/2000 | Reiley et al. | |
| 6,235,043 B1 | 5/2001 | Reiley et al. | |
| 6,241,734 B1 | 6/2001 | Scribner et al. | |
| 6,248,110 B1 * | 6/2001 | Reiley et al. .................... 606/93 |
| 6,423,083 B2 | 7/2002 | Reiley et al. | |

(Continued)

FOREIGN PATENT DOCUMENTS

DE   3922044 A1   7/1989

(Continued)

OTHER PUBLICATIONS

International Search Report mailed Jan. 19, 2007; 8 pages.

(Continued)

*Primary Examiner* — Eduardo C Robert
*Assistant Examiner* — Elana B Fisher
(74) *Attorney, Agent, or Firm* — Haynes and Boone, LLP

(57) ABSTRACT

An apparatus includes an elongate body and an expandable member coupled to the elongate body. In one embodiment, the expandable member has a collapsed configuration, an unfolded configuration and an expanded configuration. The expandable member is configured to be percutaneously inserted into an interior portion of a bone structure when the expandable member is in the collapsed configuration. The expandable member is configured to exert a pressure in a vertical direction on a first portion of the bone structure in contact with the expandable member greater than a pressure exerted in a lateral direction on a second portion of the bone structure in contact with the expandable member when the expandable member transitions from the unfolded configuration to the expanded configuration.

22 Claims, 10 Drawing Sheets

U.S. PATENT DOCUMENTS

| | | |
|---|---|---|
| 6,607,544 B1 | 8/2003 | Boucher et al. |
| 6,632,235 B2 | 10/2003 | Weikel et al. |
| 6,663,647 B2 | 12/2003 | Reiley et al. |
| 6,706,069 B2 | 3/2004 | Berger |
| 6,740,093 B2 | 5/2004 | Hochschuler et al. |
| 6,852,095 B1 | 2/2005 | Ray |
| 6,960,215 B2 | 11/2005 | Olson, Jr. et al. |
| 6,979,341 B2 | 12/2005 | Scribner et al. |
| 6,981,981 B2 | 1/2006 | Reiley et al. |
| 7,044,954 B2 | 5/2006 | Reiley et al. |
| 7,153,306 B2 * | 12/2006 | Ralph et al. .............. 606/92 |
| 7,241,303 B2 * | 7/2007 | Reiss et al. .............. 606/192 |
| 2003/0220649 A1 * | 11/2003 | Bao et al. .............. 606/90 |
| 2004/0092948 A1 * | 5/2004 | Stevens et al. .............. 606/96 |
| 2005/0090852 A1 | 4/2005 | Layne et al. |
| 2005/0209595 A1 | 9/2005 | Karmon |
| 2005/0234498 A1 * | 10/2005 | Gronemeyer et al. ........ 606/192 |

FOREIGN PATENT DOCUMENTS

| | | |
|---|---|---|
| JP | 8038618 | 2/1996 |
| WO | 9856301 | 12/1998 |
| WO | WO 02/085227 A1 | 10/2002 |
| WO | WO 2004/012614 A2 | 2/2004 |
| WO | WO 2004/043303 A2 | 5/2004 |
| WO | WO 2005/027734 A2 | 3/2005 |
| WO | WO 2006/034436 A2 | 3/2006 |

OTHER PUBLICATIONS

Shutov et al., Cellular UHMW Polyethylene Produed by Non-Foaming Leaching Technique, Journal of Cellular Plastics, vol. 38, No. 2, 163-176 (2002) Abstract.

* cited by examiner

LOW-COMPLIANCE EXPANDABLE MEDICAL DEVICE

CROSS-REFERENCE TO RELATED APPLICATION

This application claims priority to U.S. Provisional Application No. 60/683,803 entitled "Low-Compliant Expandable Medical Device," filed May 24, 2005, the disclosure of which is incorporated herein by reference in its entirety.

BACKGROUND

The invention relates generally to medical devices and procedures, and more particularly to a low-compliance expandable medical device for use in medical procedures. For example, the medical device may be inserted inside a bone structure to create a cavity.

Inflatable devices are used in a variety of medical procedures. Many inflatable medical devices are constructed with elastic or highly-compliant materials that allow the inflatable medical devices to expand within the particular space in which they are deployed. The expansion path of the inflatable medical device and the expanded shape of the device can at times be unpredictable, as the device will typically expand within the space provided in a path of least resistance. For example, for portions of a patient's body having a non-uniform hardness, an inflatable medical device may not expand in a predictable manner.

Thus, a need exists for different types of expandable medical devices and methods for compacting or compressing tissue (e.g., bone or soft tissue) within an interior area of a body of a patient.

SUMMARY OF THE INVENTION

Apparatuses and methods for performing minimally-invasive medical procedures are disclosed herein, In one embodiment, an apparatus includes an elongate body and an expandable member coupled to the elongate body. The expandable member has a collapsed configuration, an unfolded configuration and an expanded configuration. The expandable member is configured to be percutaneously inserted into an interior portion of a tissue (e.g., bone or soft tissue) or an organ such as a vertebral body, when the expandable member is in the collapsed configuration. The expandable member is configured to exert a greater pressure in a vertical direction than in a lateral direction when expanded. For example, the expandable member can be configured to exert a pressure in a vertical direction on a portion of a vertebral body that is in contact with the expandable member. The pressure in the vertical direction is greater than a pressure exerted in a lateral direction on a portion of the vertebral body in contact with the expandable member when the expandable member transitions from the unfolded configuration to the expanded configuration.

BRIEF DESCRIPTION OF THE DRAWINGS

The invention is described with reference to the accompanying drawings. In the drawings, like reference numbers indicate identical or functionally similar elements.

DETAILED DESCRIPTION

Figure 1:
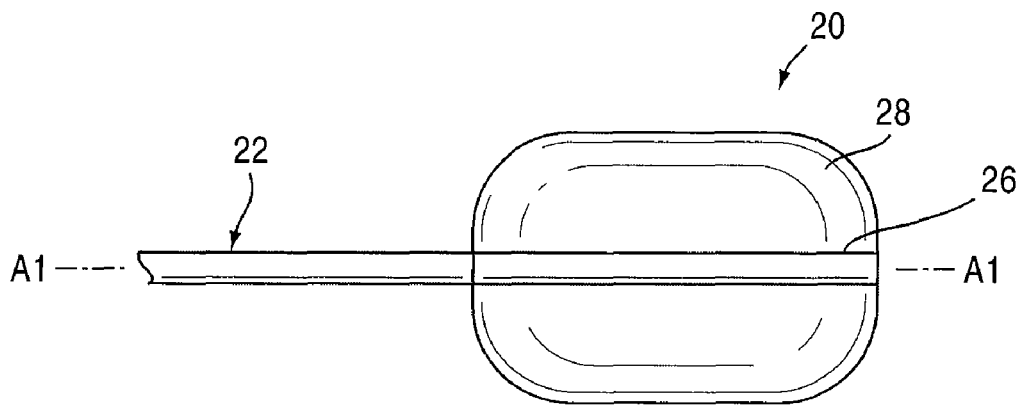
FIG. 1 is a side view of a medical device according to an embodiment of the invention shown in an expanded configuration.

In at least some embodiments, the medical devices described herein are configured for percutaneous deployment within an interior area of a patient's body, such as within a bone structure or soft tissue area of a patient. For example, a medical device according to an embodiment of the invention may include an expandable member configured to compact and forcibly displace bone material (e.g., cancellous bone) within a bone structure, such as a vertebra, of the patient when expanded. A medical device according to an embodiment of the invention may also include an expandable member configured to be movably disposed within a cannula.

Note that, as used in this specification and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the catheter end inserted inside the patient's body would be the distal end of the catheter, while the catheter end outside the patient's body would be the proximal end of the catheter.

In one variation, an apparatus includes an elongate body and an expandable member coupled to the elongate body. The expandable member has a collapsed configuration, an unfolded configuration and an expanded configuration. The expandable member is configured to be percutaneously inserted into an interior portion of a bone structure when the expandable member is in the collapsed configuration. The expandable member when in the expanded configuration is configured to exert a pressure in a vertical direction on a first portion of the bone structure in contact with the expandable member greater than a pressure exerted in a lateral direction on a second portion of the bone structure in contact with the expandable member when the expandable member transitions from the unfolded configuration to the expanded configuration.

In another embodiment, an apparatus includes an elongate body and an expandable member constructed with low-compliance material releasably coupled to the elongate body. The expandable member has a collapsed configuration and an expanded configuration. The expandable member is configured to be percutaneously disposed entirely within an interior portion of a single vertebral body. The expandable member in the expanded configuration is configured to be released from the elongate body and remain within the interior portion of the vertebral body after the elongate body has been removed from the vertebral body.

In yet another embodiment, an apparatus includes an elongate body that defines a longitudinal axis, and an expandable member constructed with low-compliance material. The expandable member is configured to be disposed within an interior portion of a vertebral body. The expandable member has a collapsed configuration and an expanded configuration. The expandable member when in the expanded configuration has a width substantially perpendicular to the longitudinal axis and greater than a length substantially parallel to the longitudinal axis. The expandable member when in the expanded configuration is configured to exert a pressure on cancellous bone disposed between the expandable member and an endplate of the vertebral body.

In one embodiment, an expandable member, when in the expanded configuration, is configured to exert forces in the inferior-superior direction within a collapsed vertebral body to restore the endplates to a proper anatomical position. The expandable member is configured to undergo highly constrained expansion in a lateral direction to prevent undesired force exertion on the lateral cortices of the vertebral body.

The term "expandable member" is used here to mean a component of the medical device that is configured to be changed or moved from a collapsed configuration to an expanded configuration in which the expandable member is larger than in the collapsed configuration. The expandable member can be expanded, for example, by introducing a medium such as fluid and/or gas into the interior of the expandable member. The expandable member can be, for example, a balloon configured to expand from a collapsed configuration to an expanded configuration.

The term "cannula" is used here to mean a component of the medical device having one or more channels configured to receive a device therethrough and provide access to an interior region of a patient's body. For example, the cannula can be substantially tubular. The cannula can be a variety of different shapes and size, such as having a round or octagonal outer perimeter, and can include any suitable number of channels. In addition, the channel(s) can be a variety of different shapes and sizes, such as square, round, triangular, or any other suitable shape.

The term "elongate body" is used here to mean a component of the medical device that is coupled to the expandable member. The elongate body can be a variety of different shapes and size, such as having a round or octagonal outer perimeter and can include one or more channels. Alternatively, the elongate body can be solid (i.e., no channels). The elongate body can also be configured to provide the means to expand the expandable member with fluid or gas. The elongate body can be, for example, a catheter.

Figure 2:
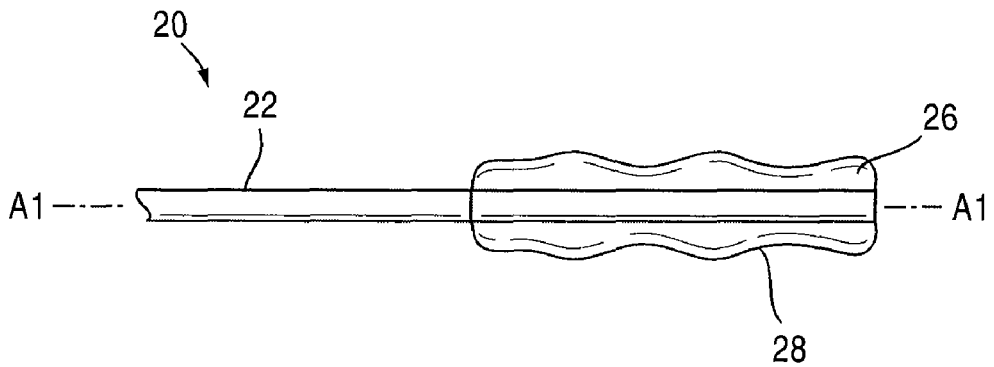
FIG. 2 is a side view of the medical device of FIG. 1 shown in a collapsed configuration.

FIG. 1 is a side view of a medical device 20 according to an embodiment of the invention. Medical device 20 includes an elongate body 22 having a proximal end portion (not shown) and a distal end portion 26. An expandable member 28 is coupled to the distal end portion 26 of the elongate body 22. The elongate body 22 defines a longitudinal axis A1 and can be configured to provide, for example, fluid or gas to expandable member 28. In some embodiments, the expandable member 28 is configured to be expanded with a solid material such as, for example, bone chips. The expandable member 28 can be moved between a collapsed configuration, as shown in FIG. 2, and an expanded configuration, as shown in FIG. 1. In the collapsed configuration, the medical device 20 can be percutaneously inserted into a patient's body. The expandable member 28 can be expanded by introducing gas, fluid, solids or other suitable material into an interior area of the expandable member. In one embodiment, the expandable member 28 is configured to expand a greater distance in a direction substantially perpendicular to the axis A1 than in a direction substantially parallel to the axis A1.

Figure 3:
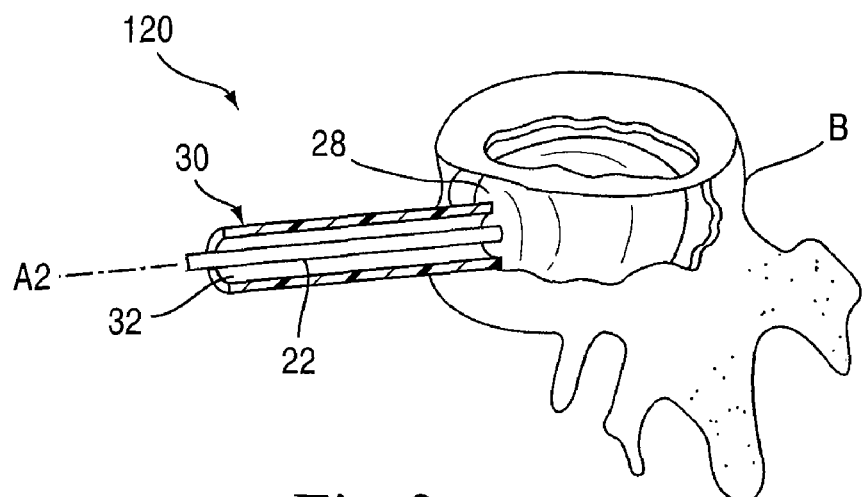
FIG. 3 is a partial cross-sectional side perspective view of a medical device according to an embodiment of the invention shown within a side perspective view of a vertebral body having a cut-away portion.

In an alternative embodiment, a medical device according to an embodiment of the invention can also include a cannula 30, such as medical device 120 shown in FIG. 3. The cannula 30 defines an axis A2 and can include one or more channels 32 in which the elongate body 22 and the expandable member 28 can be movably disposed when the expandable member 28 is in the collapsed configuration. The cannula 30 is configured to provide percutaneous access to an interior portion of a patient through the channel 32. For example, the cannula 30 can be used to provide access to an interior portion of a bone structure, such as a vertebral body B of a patient as shown in FIG. 3, to perform a medical procedure within the bone structure.

The expandable member 28 is constructed with a low-compliance material, which provides the expandable member 28 with more predictable expanding characteristics than inflatable devices constructed with high-compliance materials.

Because the expandable member 28 is constructed with low-compliance materials, the expandable member 28 can be configured such that it will expand in a predictable manner. For example, the expandable member can be configured to expand to a predetermined profile (shape and size), in a predetermined direction. The expandable member 28 can also have a predetermined pressure in an unfolded configuration, a predetermined compressive stress or exerted pressure in an expanded configuration, and a predetermined expansion height. Thus, the expandable member 28 can be pre-calibrated for the particular body area, type of body composition (e.g., soft or hard bone, soft or hard tissue, or a region of bone or tissue having varying hardness through the region) and type of procedure to be performed. The low-compliance material of the expandable member 28 is also more puncture resistant, as well as monomer resistant, than a high-compliance material. In some embodiments, the expandable member 28 can be constructed with low-compliance material having varying compliancy as a function, for example, of time and/or temperature.

Figure 4:
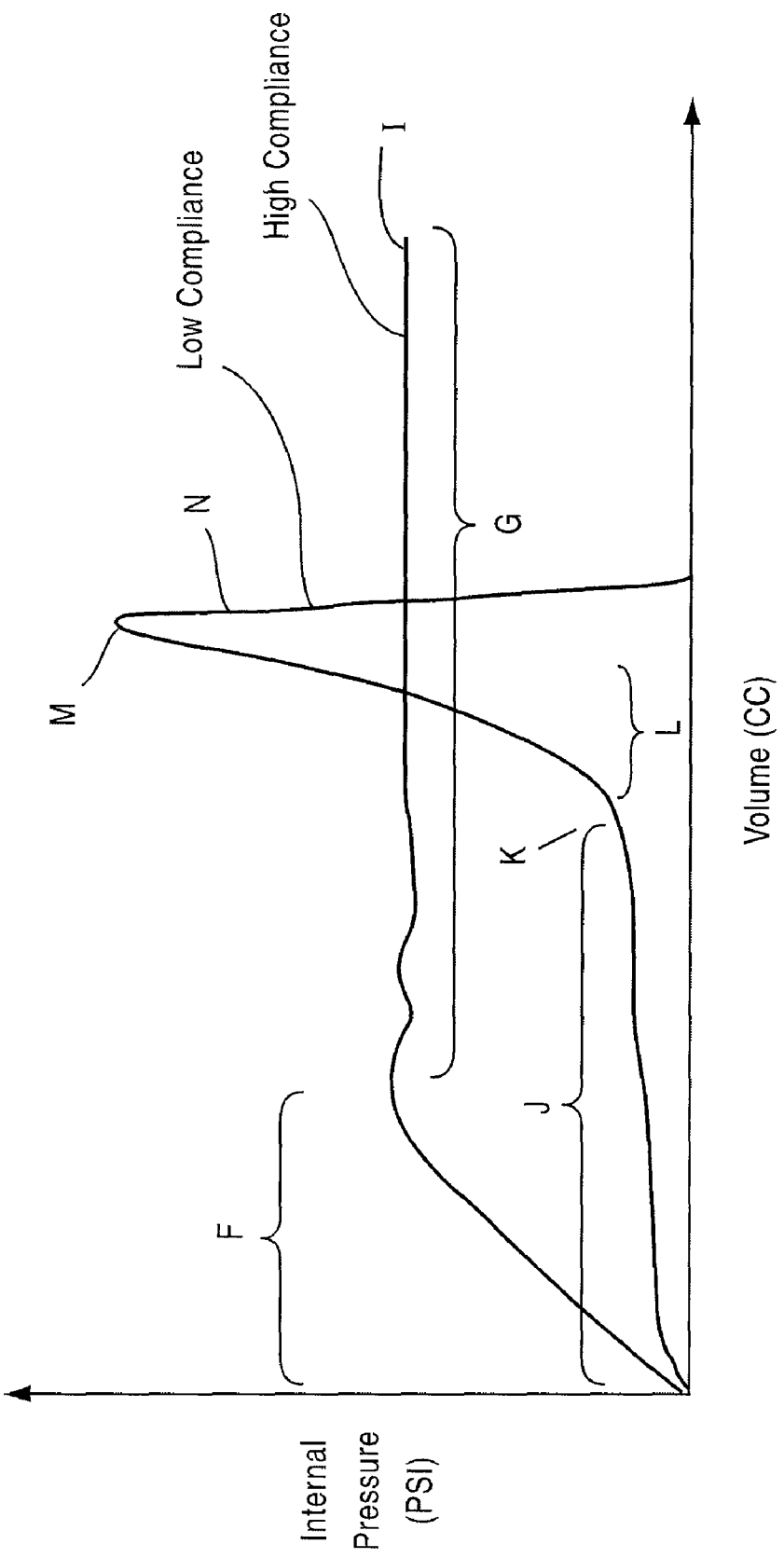
FIG. 4 is an example of a graph of the expansion pressures and inflation volumes for a high-compliance balloon and a low-compliance balloon in a uniform surrounding medium.

A low-compliance balloon, such as expandable member 28, has different performance characteristics than a high-compliance balloon. For example, FIG. 4 illustrates an example graph comparing pressure vs. volume during expansion of a low-compliance balloon and a high-compliance balloon within a uniform surrounding medium (e.g., air). The vertical axis is the pressure (measured in pounds per square inch (psi)) within the interior of the balloon. The pressure the balloon exerts on the surrounding medium may be the same or different from the pressure within the interior of the balloon depending upon the situation. For example, the pressure the balloon exerts on the surrounding medium can be the same as the pressure in the interior of the balloon when the balloon is expanded at a substantially constant rate. In addition, in situations where the balloon is expanded in a non-uniform medium, the pressure exerted on the medium may be different at different portions of the medium. For example, in relatively softer bone or tissue structures the pressure may be relatively low, and in relatively harder bone structures the pressure may be relatively high.

The horizontal axis of the graph illustrated in FIG. 4 is the inflation volume (measured in cubic centimeters (cc)) within the balloons as they are inflated. As shown in the graph, the pressure of a high-compliance balloon increases quickly as the balloon unfolds or starts to expand (region F), then levels off to a substantially constant pressure (region G) as more volume is introduced into the balloon. Because a high-compliance balloon stretches as the volume introduced into the balloon increases, the pressure remains relatively constant once the high-compliance balloon is unfolded. As more volume is introduced, instead of pressure building up within the balloon, the balloon stretches to accommodate the increased volume. Thus, after a high-compliance balloon is fully unfolded (point H) the pressure is substantially the same as when the high-compliance balloon is fully expanded (point I).

In contrast, the pressure of a low-compliance balloon will increase at a slow rate initially as the balloon unfolds (region J). When the low-compliance balloon is substantially unfolded (point K), the pressure will be relatively low. For example, during the unfolding, when the balloon is partially unfolded and without contacting an obstruction, the balloon can exert a relatively low pressure in a lateral and/or vertical direction. When the balloon encounters an obstruction (i.e., a material or portion harder than another material or portion within the surrounding medium), however, the balloon can exert a relatively low pressure in one direction (e.g., the horizontal direction (lateral or longitudinal) and a relatively high pressure in a different direction (e.g., the vertical direction). In such a case, the balloon can be, for example, fully unfolded in the lateral direction and only partially unfolded in the vertical direction. Here, the balloon transitions from the unfolded configuration to the expanded configuration in the sense that lateral expansion is limited by the low-compliance material of the balloon and vertical expansion is limited by the obstruction. In other cases, the balloon transitions from the unfolded configuration to the expanded configuration when the balloon is fully unfolded and additional volume is introduced into the balloon.

As shown in FIG. 4, once fully or substantially unfolded, as more volume is introduced into the balloon, the pressure will increase (region L) to a maximum level (point M) in which the balloon is in a substantially expanded configuration. For example, during the expanding from the fully unfolded configuration to the expanded configuration, the balloon can exert a relatively high pressure on the surrounding medium. During this transition and once at the maximum level (fully expanded), the balloon may only be able to expand or stretch some nominal amount (e.g., approximately 5%) before bursting. Because a low-compliance balloon is only able to stretch a minimal amount, the low-compliance balloon exerts a relatively high pressure for a very short period of time and then drops to a substantially zero pressure when it burst as shown on the graph at region N.

In some embodiments, the predetermined shape and size of a low-compliance balloon can be selected so that when the balloon is substantially unfolded within a bone structure or other tissue, it will be positioned adjacent to a region of bone or tissue having a relatively hard portion that a medical practitioner seeks to compress, move or break. By fully expanding the balloon to an expanded configuration when adjacent to such a hard region of bone or tissue, the hard region of bone or tissue will be subject to a relatively high pressure of the expanding balloon (see, for example, region L of FIG. 10). As a result, a relatively high pressure can be applied to a desired region of bone or tissue with minimal risk that the low-compliance balloon will expand into an undesired direction or distance (e.g., through a vertebral endplate or cortical lateral wall).

An expandable member 28 can be constructed and calibrated such that the expandable member 28 has sufficient strength and can apply sufficient pressure to break through relatively harder bone (e.g., recalcitrant fractures, sclerotic bone, cortical bone). An expandable member 28 can also be constructed and calibrated such that the expandable member 28 has lower exertion pressures for use in softer bone and tissue areas. An expandable member 28 can be constructed and calibrated such that it expands vertically a greater distance than it expands laterally, and can be constructed and calibrated to expand to a variety of different profiles (shapes and sizes), including a variety of different expansion heights and/or widths. Thus, a variety of different low-compliance expandable members 28 can be constructed having a variety of different calibrations.

Figure 5:
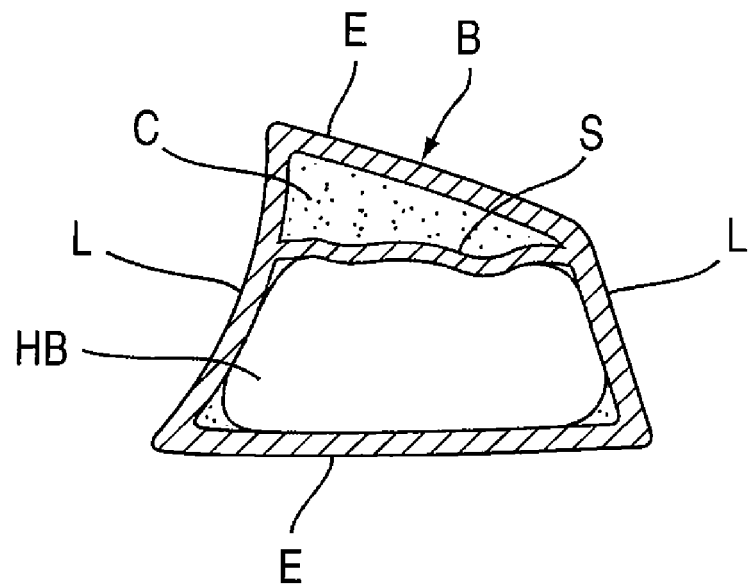
FIG. 5 is a side view of an example of a high-compliance balloon device in an expanded configuration shown positioned within a cross-sectional view of a bone structure.

In an exemplary application of the medical device 20 (120) according to an embodiment of the invention, the medical device 20 (120) is used to repair a collapsed vertebral body. As shown in FIGS. 5-9, which illustrate cross-sectional views of a vertebral body B, an upper endplate E of the vertebral body B may become damaged or collapsed, for example, by a fracture in a cortical lateral wall L causing the upper endplate E to partially collapse. Known medical procedures can be performed to raise the upper endplate E and restore the vertebral height using one of a variety of different expandable devices. An interior portion of the vertebral body B may also become damaged during or after the collapse of the upper endplate E. After the damage has healed, a portion of the interior of the vertebral body B may form a scarred bone area, known as sclerotic bone S, as shown in FIGS. 5-9. The sclerotic bone S is hard bone that a high-compliance balloon may, in certain circumstances, be unable to penetrate or compact upon expansion within the vertebral body B. The soft cancellous bone within the interior of a vertebral body can be compacted with approximately 5 MPa of pressure, whereas as sclerotic bone may require approximately 80 MPa. A typical high-compliance balloon may be unable to push through the sclerotic bone S, and will instead expand in a path of least resistance, such as expanding laterally and/or downwardly within the vertebral body B, as shown in FIG. 5. FIG. 5 illustrates an example of a high-compliance balloon HB that has expanded within the vertebral body B in a path of least resistance. This type of expansion within a vertebral body can, in this example, increase the risk of the balloon fracturing the lower endplate E or lateral walls L of the vertebral body B. In such a case, a high-compliance balloon will not be able to penetrate through the sclerotic bone S to gain access to the collapsed upper endplate E.

Figure 6:
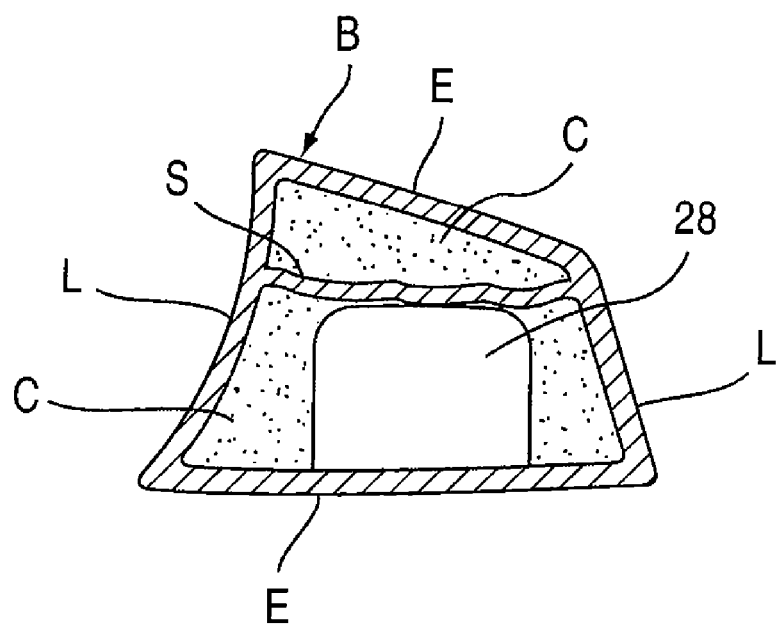
FIG. 6 is a side view of a portion of a medical device according to an embodiment of the invention in an expanded configuration and shown positioned within a cross-sectional view of a bone structure.
Figure 7:
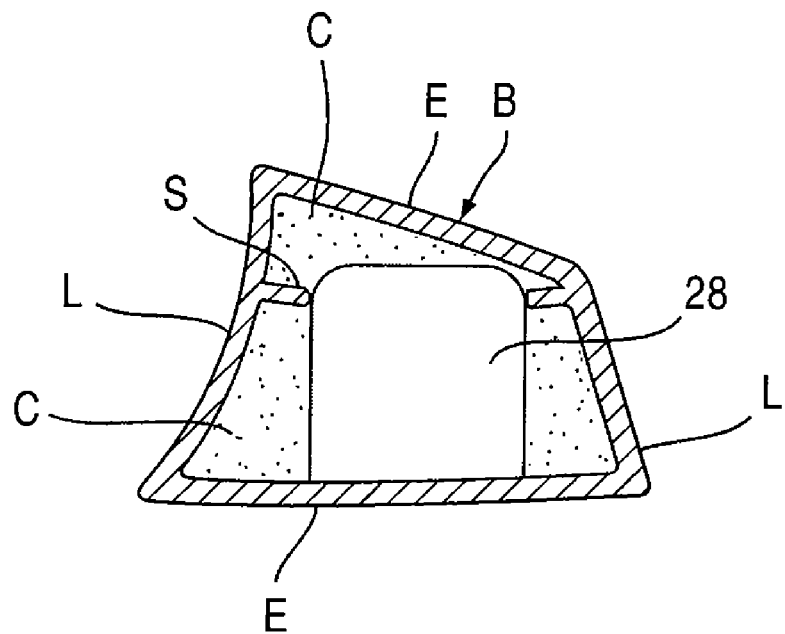
FIG. 7 is a cross-sectional view of the bone structure of FIG. 6 with the medical device shown expanded through a portion of sclerotic bone within the bone structure.
Figure 8:
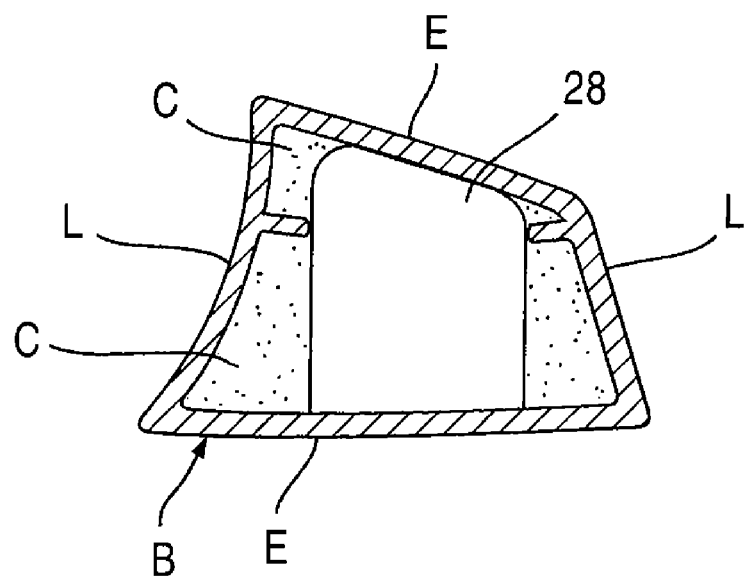
FIG. 8 is a cross-sectional view of the bone structure of FIG. 6 with the medical device shown expanded into contact with the upper end plate of the bone structure.
Figure 9:
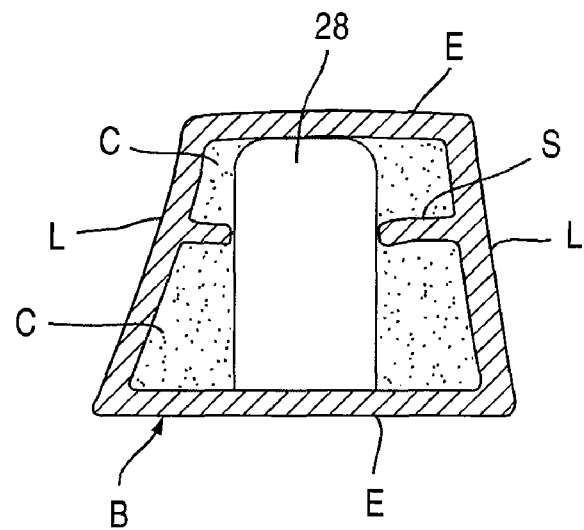
FIG. 9 is a cross-sectional view of the bone structure of FIG. 6 with the medical device shown expanded vertically such that the upper/superior endplate of the bone structure is moved upward.

A low-compliance expandable member 28 described herein can be configured, for example, to penetrate through the sclerotic bone S and gain access to the upper endplate E, as shown in FIGS. 6-9. Thus, the risk of fracturing or breaking through the lower endplate or lateral walls of the vertebral body during expansion of the expandable member is substantially reduced. In one embodiment, a first medical device 20 (120) can be selected having an expandable member 28 with selected calibration parameters, such as expansion height, expansion profile, and expansion pressure, to allow it to penetrate through the sclerotic bone S. The first medical device 20 (120) can be inserted into the vertebral body B and the expandable member 28 expanded to an unfolded configuration in which it exerts pressure and compacts at least a portion (e.g., a lower portion below the sclerotic bone) of the cancellous bone C within the vertebral body B, as shown in FIG. 6. Thus, a cavity can be created within the interior of the vertebral body B below the sclerotic bone S. Such a cavity may be created, for example, for insertion of bone cement or other suitable material into the cavity. The expandable member 28 can then be expanded to an expanded configuration in which it exerts a greater pressure than in the unfolded configuration such that the sclerotic bone S is penetrated or broke-through, as shown in FIG. 7. The expandable member 28 can then be expanded further such that it expands in a vertical direction and contacts the upper end plate as shown in FIG. 8. The upper endplate E will be moved upwardly reducing the fracture and restoring at least a portion of the vertebral height, as shown in FIG. 9. In some situations, the original vertebral height will be restored. As an alternative to the above procedure, after the expandable member 28 has broke through the sclerotic bone, a second medical device 20 (120) having a differently calibrated expandable member can be inserted into the vertebral body B and expanded such that it contacts the upper endplate E. The second expandable member can be further expanded such that the expandable member forces the upper endplate E to be moved upwardly reducing the fracture and restoring at least a portion of the vertebral height.

The second medical device 20 (120) may be calibrated such that it expands vertically a greater distance than the first medical device 20 (120) allowing it to contact the upper endplate E. In addition, because the second medical device 20 (120) is being deployed after the sclerotic bone S has been broke-through, the required expansion pressure of the second medical device 20 (120) can be less than what was required of the first medical device 20 (120). For example, the second medical device 20 (120) may compact cancellous bone above the sclerotic bone S, while exerting a relatively low pressure during the unfolding. Because the second medical device 20 (120) does not have to penetrate sclerotic bone, the second medical device 20 (120) can alternatively have an expandable member constructed with high-compliance material.

In the embodiment described above with reference to FIGS. 6-9, where only one medical device 20 (120) is used, the expandable member 28 can be formed with sufficient calibration parameters to allow the expandable member 28 to penetrate the sclerotic bone within a vertebral body. The expandable member 28 can be constructed and calibrated with a size and pressure such that it can penetrate the sclerotic bone and expand to a sufficient vertical height while expanding to the expanded configuration. The use of only one medical device 20 (120) may also be sufficient where the pressure needed to break through sclerotic bone S is such that unfolding is sufficient.

Figure 10:
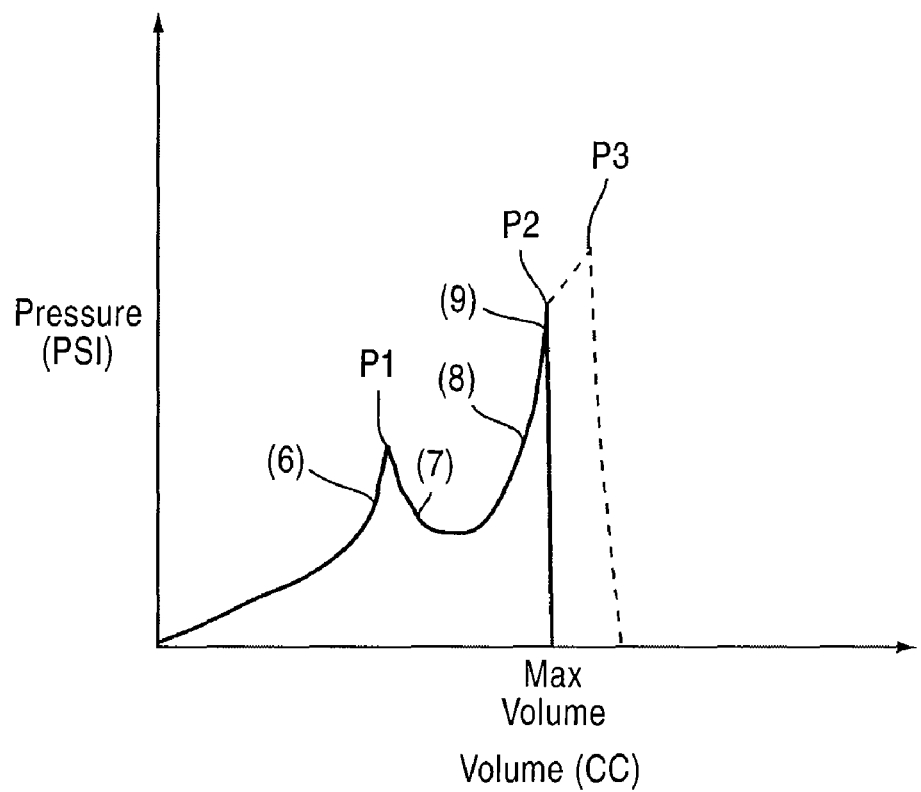
FIG. 10 is an example of a graph illustrating expansion pressures and inflation volumes associated with the expansion of a low-compliance expandable member within a bone structure.

FIG. 10 is a graphical representation of an example of the interior inflation pressures and volumes of a low-compliance expandable member as it is expanded within a non-uniform medium such as a vertebral body as described above with reference to FIGS. 6-9. Regions 6, 7, 8, and 9 on the graph represent the interior volume and pressure that corresponds to the expansion of the expandable member 28 illustrated in FIGS. 6-9, respectively. As the expandable member is being unfolded within the vertebral body, the expandable member will have a relatively small interior volume and a relatively low interior pressure, as indicated at region 6 in FIG. 10. When the expandable member contacts the sclerotic bone, the pressure within the expandable member will build up to a peak pressure indicated at P1 until the expandable member breaks through the sclerotic bone. At the time the expandable member breaks through the sclerotic bone, the pressure within the expandable member will drop as indicated at region 7 on the graph. As the expandable member is further expanded within the vertebral body, the interior pressure will again begin to increase, as shown at region 8, until it reaches a relatively high pressure as indicated at region 9. If the expandable member were to continue to be expanded, the expandable member would eventually reach a maximum volume and corresponding maximum pressure P2. If the expandable member is expanded beyond the maximum volume, the expandable member will typically burst, dropping the volume and pressure to substantially zero. That said, the example contemplated by FIGS. 6-10 and typically used would not involve the balloon bursting.

A low-compliance expandable member (or balloon as hereinafter referred) can be manufactured with a variety of materials, such as PET, Nylons, cross-linked Polyethylene, Polyurethanes, and PVC that provide the balloon with the necessary characteristics to effectively compact bone material. Some parameters of low-compliance balloons include the tensile strength, the compliance, the stiffness, the profile (i.e., the relative size of the balloon when in its collapsed configuration prior to use) and the maximum rated pressure (psi) of the balloon. A comparison of various parameters for some example low-compliance balloon materials is provided in the table below. The ratings (e.g. high, medium, low) listed in the table are relative to low-compliance balloons.

| Materials | Tensile Strength | Compliance | Stiffness | Profile |
| --- | --- | --- | --- | --- |
| PET | High-Very High | Low-Medium | High | Low |
| Nylons | Medium-High | Medium | Medium | Low-Medium |
| PE cross-linked and other polyolefins | Low | High | Low | High |

-continued

| Materials | Tensile Strength | Compliance | Stiffness | Profile |
|---|---|---|---|---|
| Polyurethanes | Low-Medium | Medium-High | Low-Medium | Medium-High |
| PVC (flexible) | Low | High | Low | High |

Such parameters can also depend on structural specifications, such as balloon wall thickness and length, width and/or other dimensions of a balloon.

Low-compliance balloons can be manufactured with such processes as an extrusion process or a blow molding process. A variety of parameters can have an effect on the mechanical properties of balloons manufactured with an extrusion process. Some extrusion parameters include the temperature profile from the feeding zone of the screw to the tooling, the tooling geometry, the temperature of the cooling bath, the tubing dimensions, the distance between the tooling and the cooling bath that affects the degree of crystallization (the faster the tubing is cooled, the more amorphous (more compliant) the final product), and the rotational speed of the gear.

In a blow molding process, a variety of parameters also can influence the balloon properties, such as the temperature of the heating jaws, the pre-pressure/warm-up time, the forming pressure, and the distal and proximal stretching. Among the above balloon forming parameters, the forming pressure can be a parameter for producing a balloon with a high burst pressure. For example, increasing the forming pressure from 200 psi to 300 psi can increase the burst pressure by 30 psi and can also shorten the cycle time for manufacturing the balloon. In addition, the wall thickness is a function of the forming pressure, the forming temperature, and the warm-up time.

In some medical procedures, it may be desirable to determine the shape and/or profile of the interior of a bone structure, as well as the bone quality, prior to performing a procedure with the medical device 20 (120) described above. Typically, an imaging device, such as an X-ray or CT is used to obtain an image of the bone structure to be treated. A biopsy may also be taken to evaluate the bone quality. Using the image, a physician or other medical professional can determine the size of balloon to use for a particular medical procedure. Likewise, the biopsy may provide information on the pressure that will be required to compact an interior area of the bone.

Figure 11:
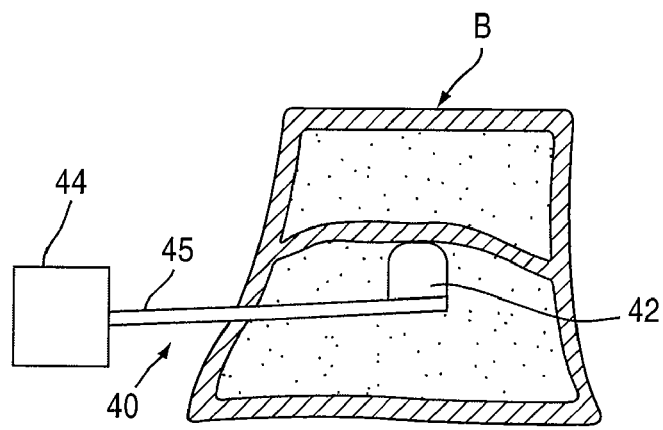
FIG. 11 is a side view of a bone probe according to an embodiment of the invention shown positioned within a cross-sectional view of a bone structure.

In another embodiment of the invention, and as an alternative to the above described procedures to evaluate the bone quality, a bone probe can be used in conjunction with the medical device 20 (120). Prior to using a medical device 20 (120), a bone probe can be deployed within the interior portion of a bone structure. As shown in FIG. 11, a bone probe 40 can include a small low-compliance expandable member (e.g., balloon) 42 as described above, coupled to a pressure indicator 44. The pressure indicator 44 can be, for example, coupled to an inflation syringe 45 that is also coupled to the balloon 42, as shown schematically in FIG. 11. As the balloon 42 is expanded within the interior area of a bone structure (or other interior area of the patient), the pressure indicator 44 can detect the internal pressure of the balloon 42, and transmit or output the pressure information to a location external to the patient. For example, the pressure data can be provided via a digital output, an analog output (e.g., dial indicator) or other visual pressure display. The information (e.g., pressure data) can be used to determine the bone quality (e.g., stiffness, force and/or stress). For example, the higher the pressure within the balloon, the stronger the bone quality. The bone probe 40 could also be configured to transmit location and/or size information regarding the interior area of the bone structure. The pressure required to expand the probe balloon to its maximum volume can relate to the ultimate compressive strength of the bone structure in which the balloon is disposed. This can provide information on the density of the bone within the bone structure in the particular region where, for example, height restoration and/or fracture reduction, may be desired. Such a bone probe balloon can be calibrated to correlate inflation pressure at full volume to bone compressive strength, which can then aid the physician and/or other medical professional in selecting a medical device 20 (120) having an expandable member 28 with the desired calibration parameters to perform the particular procedure.

Figure 12:
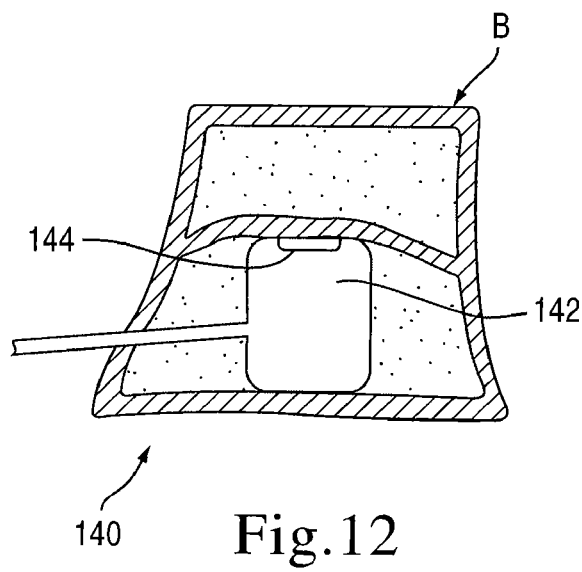
FIG. 12 is a side view of a bone probe according to an embodiment of the invention shown positioned within a cross-sectional view of a bone structure.

In another embodiment, a probe can include an expandable member and a pressure indicator coupled directly to the expandable member. As shown in FIG. 12, a probe 140 can include an expandable member 142, and a pressure indicator 144 coupled to the expandable member 142. In such an embodiment, when the probe 140 is actuated within a bone structure B, the pressure indicator 142 contacts an interior portion of the bone structure B. The pressure indicator 142 can transmit pressure data to a location exterior to the bone structure as with the previous embodiment.

Figure 13:
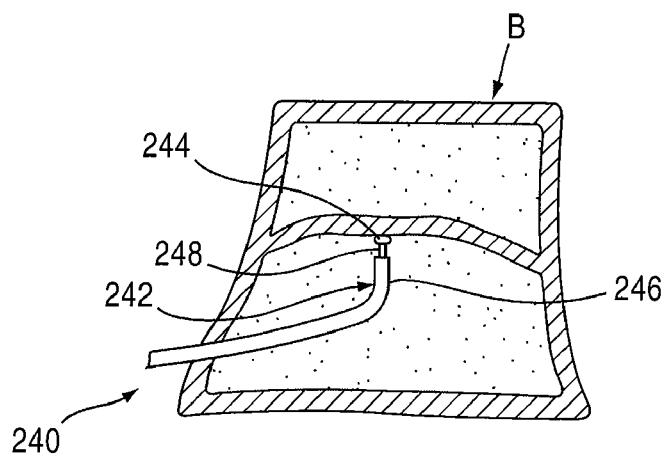
FIG. 13 is a side view of a bone probe according to another embodiment of the invention shown positioned within a cross-sectional view of a bone structure.

In an alternative embodiment, a bone probe 240 can include an expandable mechanical member 242, instead of balloon 42 or 142, as shown in FIG. 13. For example, the expandable mechanical member 242 can have a plunger body 246 having an actuating tip 248 on a distal end. The tip 248 includes a pressure indicator 244 and is configured to tap or push against the bone to determine, for example, the force, stiffness, or stress of the bone and output the information to a visual output (e.g., digital output, analog output, etc.) external to the patient, as with the previous embodiment.

Figure 14:
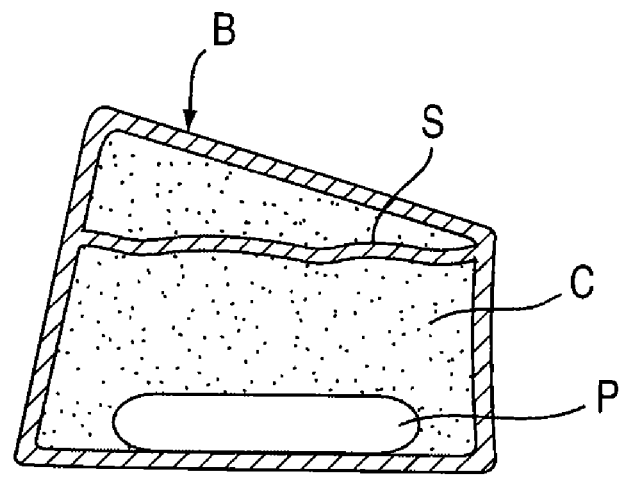
FIG. 14 is a side view of a platform portion according to an embodiment of the invention positioned within a cross-sectional view of a bone structure.
Figure 15:
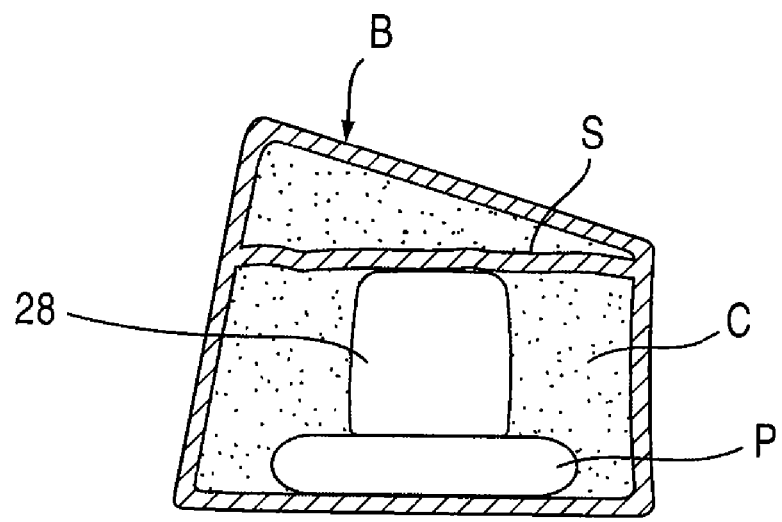
FIG. 15 is a side view of a portion of a medical device according to an embodiment of the invention positioned within a cross-sectional view of a bone structure.

In some medical procedures, for example, a procedure performed on a vertebral body, it may be desirable to perform a first procedure to create a platform within the bone structure on which a medical device 20 (120) can be supported. For example, a procedure may include inserting a device, such as a medical device 20 (120) or other suitable medical device, into the vertebral body and actuating or expanding the device such that it compacts the cancellous bone in the interior of the vertebral body and creates a cavity. Once the cavity is created, bone cement or other suitable material is introduced into the cavity to create a solid or hard platform portion P within the vertebral body B, as shown in FIG. 14. A medical device 20 (120) can then be inserted into the interior area of the vertebral body using the platform portion P as a base support, as shown in FIG. 15. This type of procedure may be desirable, for example, where it is determined that the sclerotic bone S is strong in comparison to the lower endplate E. In such a case, to ensure that the endplate E is not fractured during the expansion of the expandable member 28 of medical device 20 (120), a platform portion P may be created for added support.

In another embodiment of the invention, a kit can be provided including multiple medical devices 20 (120) and/or multiple expandable members 28. The kit can include expandable members having various constructions and calibrations. A physician or other medical professional can select from the kit the appropriate medical device(s) 20 (120) to use for the particular patient and/or procedure. The kit can include replacement expandable members 28 configured to be removably attached to a cannula and/or other medical device. In some embodiments the kit can also include one or more bone probes 42 (142). As described above, a particular medical procedure may require the use of one or more medical devices 20 (120) and or the use of a bone probe 42 (142).

A kit provides the physician or other medical professional with a variety of optional medical devices 20 (120) to select from depending on the particular procedure to be performed.

Figure 16:
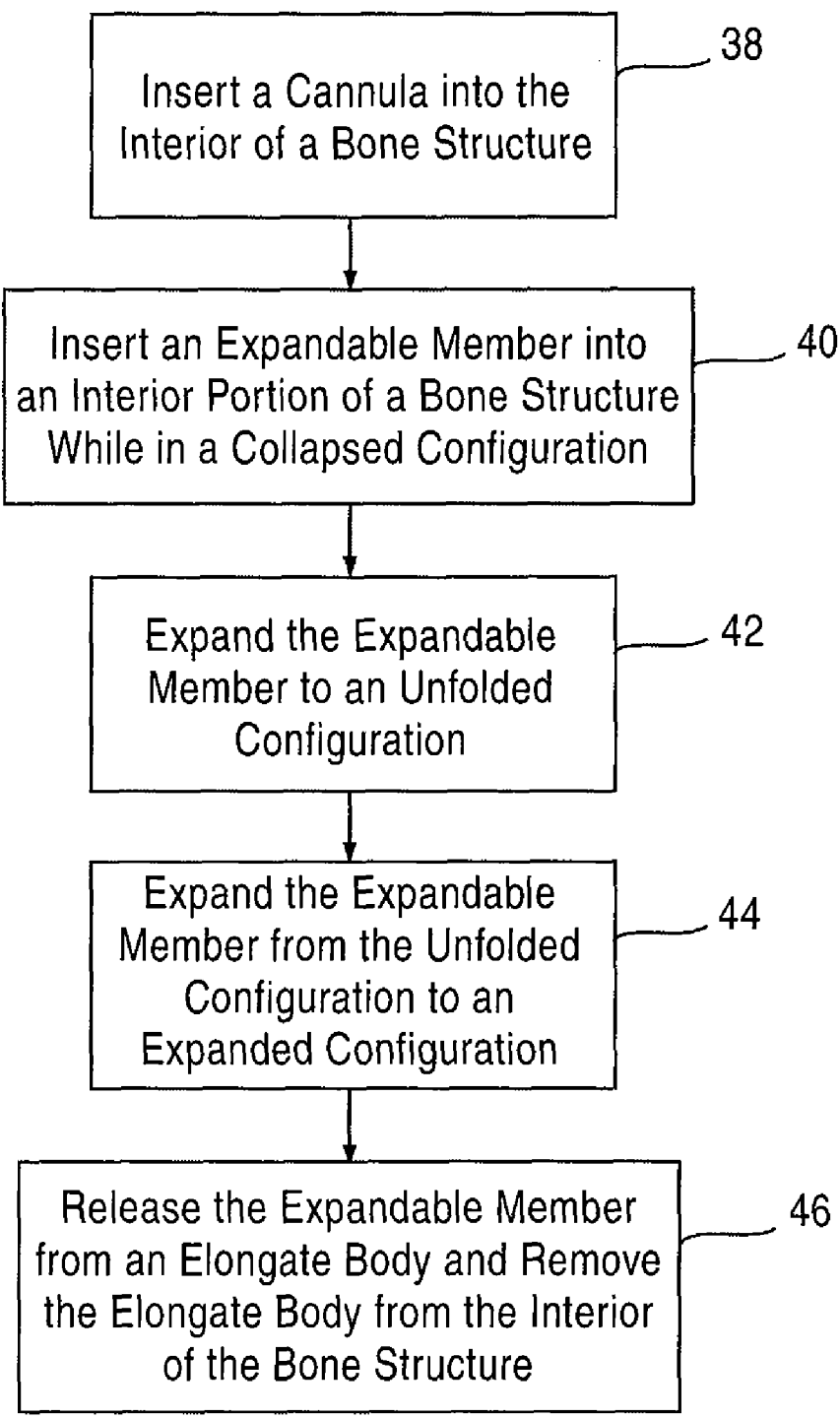
FIG. 16 is a flowchart of a method of performing a medical procedure within a bone structure according to an embodiment of the invention.

FIG. 16 is a flowchart illustrating a method of performing a medical procedure within a bone structure according to an embodiment of the invention. A method can include inserting an expandable member while in a collapsed configuration into an interior portion of a bone structure, such as a vertebral body, at 40. In some embodiments, prior to inserting the expandable member into the interior of the bone structure, a cannula can optionally be inserted into the interior portion of the bone structure at 38. The expandable member can then be inserted through the cannula when the expandable member is inserted into the interior of the bone structure. The expandable member can be constructed with a low-compliance material. The expandable member can be expanded while inserted in the interior portion of the bone structure such that the expandable member expands to an unfolded configuration at 42. At 44, the expandable member can be expanded while inserted in the interior portion of the bone structure such that the expandable member moves from the unfolded configuration to an expanded configuration and such that the expandable member exerts a pressure in a vertical direction on a first portion of the interior portion of the bone structure in contact with the expandable member greater than a pressure exerted in a lateral direction on a second portion of the bone structure in contact with the expandable member. In some embodiments, when expanding the expandable member to move the expandable member from the unfolded configuration to the expanded configuration, the expandable member expands a greater distance in a direction perpendicular to a longitudinal axis defined by the elongate body than in a direction parallel to the axis.

In some embodiments, the expandable member is releasably coupled to an elongate body. In such an embodiment, the expandable member can optionally be released from the elongate body while the expandable member is within the interior of the bone structure and the elongate body can be removed from the interior of the bone structure at 46, leaving the expandable member within the interior of the bone structure.

Figure 17:
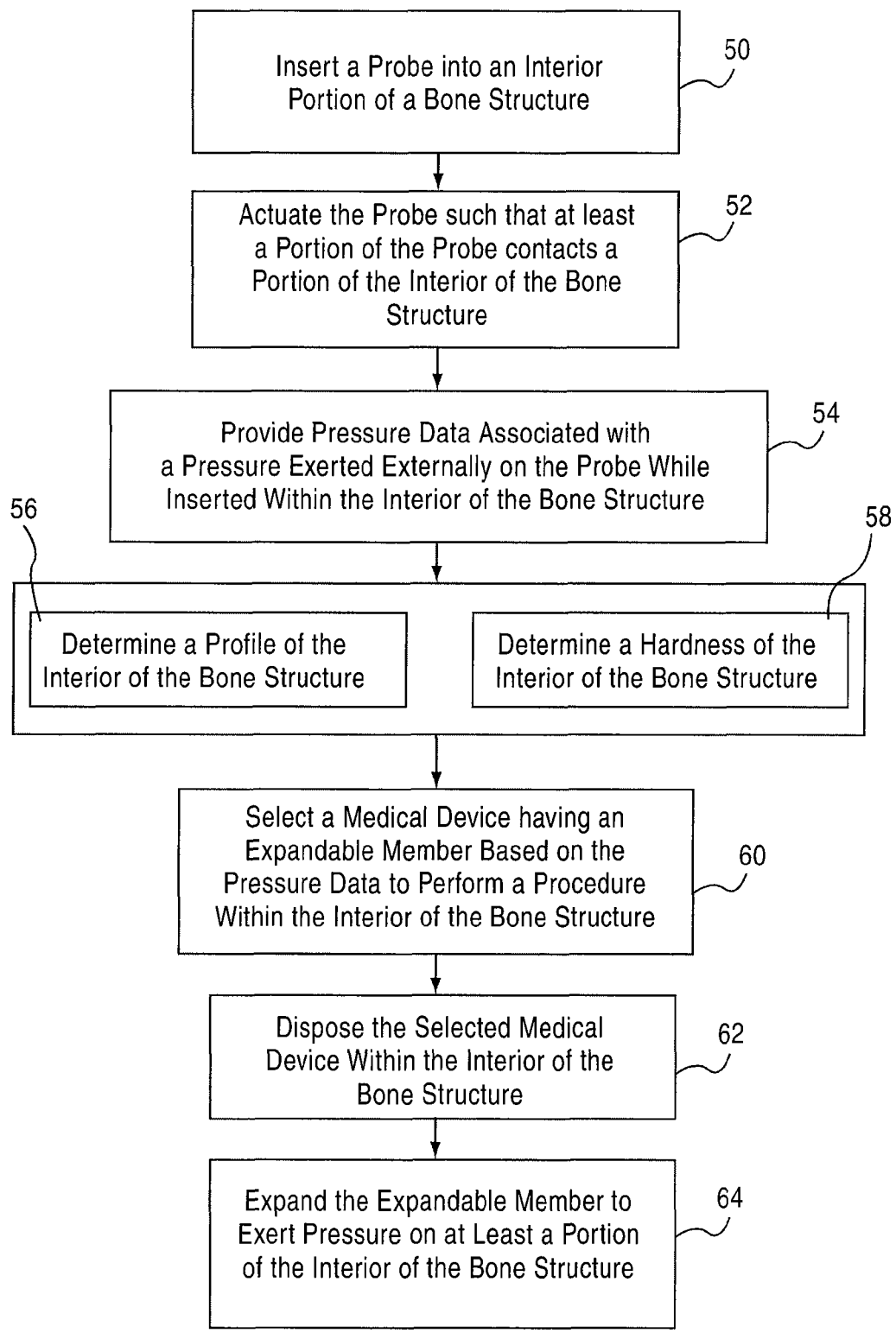
FIG. 17 is a flowchart of a method of performing a medical procedure within a bone structure according to another embodiment of the invention.

FIG. 17 is a flowchart illustrating another method for performing a medical procedure within a bone structure according to an embodiment of the invention. A method includes at 50, inserting a probe into an interior portion of a bone structure of a patient. In some embodiments, the probe can include an expandable member coupled to a pressure indicator. In some embodiments, the probe includes a body and an actuating tip movably coupled to the body. In such an embodiment, the pressure indicator can be disposed at the actuating tip. At 52, the probe can be actuated such that at least a portion of the probe contacts a portion of the interior portion of the bone structure. In some embodiments, the probe can be actuated multiple times at different locations. At 54, pressure data can be provided that is associated with a pressure exerted externally on the probe while inserted within the interior of the bone structure. At 56, a profile of the interior portion of the bones structure can optionally be determined based on the pressure data. The hardness of the interior portion of the bone structure can also optionally be determined at 58.

In some embodiments, a medical device configured to perform a procedure within the bone structure can optionally be selected based on the pressure data at 60. In some embodiments, the medical device can include an expandable member. The expandable member of the medical device can optionally be inserted into the bone structure at 62. The expandable member can optionally be expanded at 64 such that the expandable member exerts a pressure on at least a portion of the interior of the bone structure. The expandable member can have an expanded size greater than the probe.

Figure 18:
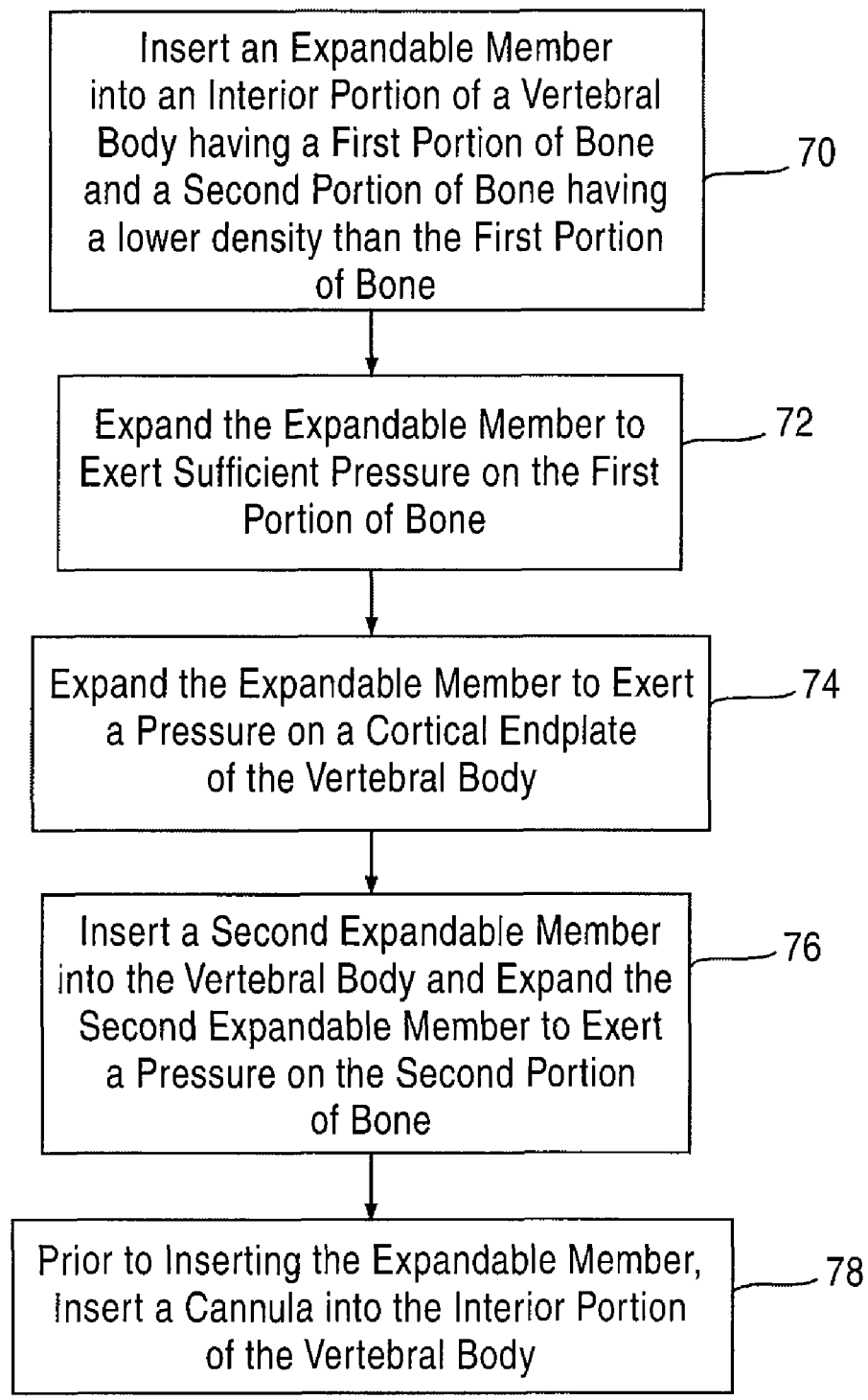
FIG. 18 is a flowchart of a method of performing a medical procedure within a vertebral body according to another embodiment of the invention.

FIG. 18 is a flowchart illustrating a method for performing a medical procedure within a vertebral body according to the invention. A method includes at 70 inserting an expandable member into an interior portion of a bone structure, such as a vertebral body, having a first portion of bone with a density and a second portion of bone with a density less than the density of the first portion. The expandable member can be constructed, for example, with a low-compliance material. The first portion of the bone is disposed apart from a cortical endplate of the vertebral body. For example, the first portion of the bone can be sclerotic, cortical or recalcitrant bone and the second portion of the bone can be cancellous bone. At 72, the expandable member can be expanded while disposed within the interior of the vertebral body such that the expandable member exerts a pressure on the first portion of bone sufficient to cause the first portion of bone to move. In some embodiments, the expandable member can be coupled to an elongate body that defines a longitudinal axis and when the expandable member is expanded it can expand a greater distance in a direction substantially perpendicular to the axis than in a direction substantially parallel to the axis. At 74, after expanding the expandable member to exert pressure on the first portion of bone, the expandable member can optionally be expanded such that the expandable member exerts pressure on an upper cortical endplate of the vertebral body. At 76, in some embodiments, prior to inserting the expandable member into the vertebral body, another expandable member can optionally be inserted into the interior portion of the vertebral body and expanded such that it exerts pressure on the second portion of bone within the vertebral body. Such an expandable member can have a set of pre-calibrated parameters different from a set of pre-calibrated parameters of the other expandable member. At 78, prior to inserting an expandable member into the vertebral body, a cannula can optionally be inserted into the vertebral body. The cannula can provide access to the interior portion of the vertebral body.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The invention has been particularly shown and described with reference to specific embodiments thereof, but it will be understood that various changes in form and details may be made.

For example, in some embodiments, the expandable member 28 may be configured to be removably coupled to the elongate body 22 such that it can be released within the interior of a bone structure of a patient and remain within the patient's body after the medical procedure has been performed. In such an embodiment, the expandable member 28 may be constructed with a low-compliance, permeable material and expanded via the insertion of bone chips as previously described. The permeability of the expandable member can allow for bone growth to occur between the bone chips and the surrounding bone structure.

In addition, more than one medical device 20 (120) may be used to perform a medical procedure. For example, a first medical device 20 (120) and a second medical device 20 (120)

can be inserted into a vertebral body and each expanded to create a cavity. The first medical device 20 (120) can be removed, while the second medical device 20 (120) remains in place within the vertebral body. Bone cement or other suitable material may then be inserted into the cavity created by the first medical device 20 (120). Thus, multiple medical devices 20 (120) can be used either simultaneously or sequentially depending on the particular procedure to be performed. Each of the medical devices 20 (120) can have an expandable member 28 constructed with either low-compliance or high-compliance material depending on the particular use of the medical device 20 (120).

What is claimed is:

1. A method comprising:
   inserting a probe comprising a pressure indicator into an interior portion of a vertebral bone structure of a vertebral body to identify a region of sclerotic bone tissue;
   inserting an expandable member while in a collapsed configuration into the interior portion of a vertebral bone structure of a vertebral body, along a longitudinal axis;
   positioning the expandable member adjacent to the region of sclerotic bone tissue;
   expanding the expandable member while inserted in the interior portion of the vertebral bone structure such that the expandable member expands to an unfolded configuration; and
   expanding the expandable member while inserted in the interior portion of the vertebral bone structure such that the expandable member moves from the unfolded configuration to an expanded configuration and such that the expandable member exerts a pressure in a vertical direction on the sclerotic bone tissue while constraining the expansion of the expandable member in a lateral direction to prevent undesired pressure exertion in the lateral direction on a second portion of the bone structure in contact with the expandable member, the pressure exerted against the region of sclerotic bone tissue being greater than the pressure exerted against the second portion of the vertebral bone structure of the vertebral body in the lateral direction;
   penetrating the region of sclerotic bone tissue within an interior portion of the vertebral bone structure of the vertebral body with the expandable member.

2. The method of claim 1, wherein the expandable member is constructed with a low-compliance material.

3. The method of claim 1, wherein when the expandable member is expanded to move the expandable member from the unfolded configuration to the expanded configuration, the expandable member expands a greater distance in a direction perpendicular to the longitudinal axis than in a direction parallel to the axis.

4. The method of claim 1, further comprising:
   prior to inserting the expandable member into the interior of the vertebral bone structure of the vertebral body, inserting a cannula into the interior portion of the vertebral bone structure of the vertebral body, the expandable member being inserted through the cannula when the expandable member is inserted into the interior of the vertebral bone structure of the vertebral body.

5. The method of claim 1, wherein the expandable member is releasably coupled to an elongate body, the method further comprising:
   releasing the expandable member from the elongate body; and
   removing the elongate body from the interior of the vertebral bone structure of the vertebral body such that the expandable member remains within the interior of the vertebral bone structure of the vertebral body.

6. The method of claim 1, wherein the expandable member is a balloon configured to expand when at least one of a fluid, a gas or a solid material is introduced into the balloon.

7. The method of claim 1, wherein an internal pressure of the expandable member is greater during the expanding the expandable member from the unfolded configuration to the expanded configuration than an internal pressure of the expandable member during the expanding the expandable member to the unfolded configuration.

8. The method of claim 1, wherein during the expanding the expandable member from the unfolded configuration to the expanded configuration the expandable member exerts a greater pressure on the interior portion of the vertebral bone structure of the vertebral body than a pressure exerted on the interior portion of the vertebral bone structure of the vertebral body when the expandable member is expanded to the unfolded configuration.

9. The method of claim 1, wherein the expandable member is configured to undergo highly constrained expansion in the lateral direction to prevent undesired force exertion on lateral cortices of the vertebra.

10. The method of claim 1, wherein the expandable member is configured to undergo highly constrained expansion in the lateral direction to prevent undesired force exertion on lateral cortices of the vertebral body and configured to exert forces in an inferior-superior direction within the vertebral body to restore an endplate to a proper anatomical position.

11. The method of claim 1 further comprising transmitting data from the pressure indicator to a location exterior of the vertebral body.

12. A method, comprising:
    inserting a probe comprising a pressure indicator into an interior portion of a vertebra to identify a region of sclerotic bone tissue;
    inserting an expandable member while in a collapsed configuration into the interior portion of a vertebra along a longitudinal axis, the expandable member constructed with a low-compliance material;
    positioning the expandable member adjacent to the region of sclerotic bone tissue;
    expanding the expandable member while inserted in the interior portion of the vertebra such that the expandable member expands to an unfolded configuration;
    expanding the expandable member while inserted in the interior portion of the vertebra such that the expandable member moves from the unfolded configuration to an expanded configuration,
    when in the expanded configuration the expandable member has a height substantially perpendicular to the longitudinal axis that is greater than a length substantially parallel to the longitudinal axis, the expandable member when in the expanded configuration configured to exert a pressure on the region of sclerotic bone tissue in the direction perpendicular to the longitudinal axis and also configured to prevent undesired pressure exertion against bone structure disposed in the direction parallel to the longitudinal axis by constraining the expansion of the expandable member; and
    penetrating the region of sclerotic bone tissue with the expandable member within the interior portion of the vertebra with the expandable member.

13. The method of claim 12, further comprising:
    prior to the inserting, inserting a cannula into the interior portion of the vertebra, the expandable member being inserted through the cannula when the expandable member is inserted into the interior of the vertebra.

14. The method of claim 12, wherein the expandable member is releasably coupled to an elongate body, the method further comprising:
    after the expanding, releasing the expandable member from the elongate body; and
    removing the elongate body from the interior portion of the vertebra such that the expandable member remains within the interior portion of the vertebra.

15. The method of claim 12, wherein during the expanding to the expanded configuration, the expandable member moves at least a portion of cancellous bone disposed between the expandable member and an endplate of the vertebra.

16. The method of claim 12, wherein the expandable member is releasably coupled to an elongate body, the method further comprising:
    after the expanding to the expanded configuration, releasing the expandable member from the elongate body; and
    removing the elongate body from the interior portion of the vertebra such that the expandable member remains within the interior portion of the vertebra, the expandable member being permeable and configured to permit bone growth between at least a portion of the interior portion of the vertebra and the expandable member while remaining disposed within the interior portion of the vertebra.

17. The method of claim 12, wherein the expandable member is a balloon configured to expand when at least one of a fluid, a gas or a solid material is introduced into the balloon.

18. The method of claim 12, wherein an internal pressure of the expandable member is greater during the expanding the expandable member from the unfolded configuration to the expanded configuration than an internal pressure of the expandable member during the expanding the expandable member to the unfolded configuration.

19. The method of claim 12, wherein during the expanding the expandable member from the unfolded configuration to the expanded configuration the expandable member exerts a greater pressure on the cancellous bone disposed between the expandable member and the endplate of the vertebra than a pressure exerted on the cancellous bone disposed between the expandable member and the endplate of the vertebra when the expandable member is expanded to the unfolded configuration.

20. The method of claim 12, wherein the expandable member is configured to undergo highly constrained expansion in the direction parallel to the longitudinal axis to prevent undesired force exertion on lateral cortices of the vertebra.

21. The method of claim 12, wherein the expandable member is configured to undergo highly constrained expansion in the direction parallel to the longitudinal axis to prevent undesired force exertion on lateral cortices of the vertebra and configured to exert forces in an inferior-superior direction within the vertebra to restore an endplate to a proper anatomical position.

22. The method of claim 12 further comprising transmitting data from the pressure indicator to a location exterior of the vertebra.

* * * * *